(12) United States Patent
Yoon et al.

(10) Patent No.: US 8,329,165 B2
(45) Date of Patent: Dec. 11, 2012

(54) COMPOSITION FOR THE TREATMENT OF BALLAST WATER CONTAINING BACTERIOPHAGE AS AN EFFECTIVE COMPONENT AND BIOLOGICAL METHOD WITH THE SAME FOR REMOVING BACTERIA PRESENT IN BALLAST WATER

(75) Inventors: Seongjun Yoon, Seoul (KR); Sooyoun Jun, Seoul (KR); Sanghyeon Kang, Seoul (KR); Yunjaie Choi, Seoul (KR); Jeesoo Son, Seoul (KR)

(73) Assignee: Intron Biotechnology, Inc., Sungnam-Si (KR)

( * ) Notice: Subject to any disclaimer, the term of this patent is extended or adjusted under 35 U.S.C. 154(b) by 972 days.

(21) Appl. No.: 12/231,691

(22) Filed: Sep. 5, 2008

(65) Prior Publication Data

US 2009/0304638 A1    Dec. 10, 2009

(30) Foreign Application Priority Data

Jun. 9, 2008  (KR) ..................... 10-2008-0053743

(51) Int. Cl.
  *A01N 63/00* (2006.01)
  *C12N 7/00* (2006.01)
  *C12N 7/01* (2006.01)
(52) U.S. Cl. .................................. 424/93.6; 435/235.1
(58) Field of Classification Search ........................ None
  See application file for complete search history.

(56) References Cited

U.S. PATENT DOCUMENTS

2004/0241825 A1* 12/2004 Mandeville et al. ....... 435/252.3
2007/0010001 A1*  1/2007 Bujanover ................. 435/235.1

FOREIGN PATENT DOCUMENTS

| KR | 100350409 | 8/2002 |
| KR | 1020030004129 | 1/2003 |
| KR | 1020030069175 | 8/2003 |
| KR | 1020050104001 | 11/2005 |
| KR | 100597254 | 6/2006 |
| KR | 100776205 | 11/2007 |
| KR | 100781669 | 11/2007 |
| KR | 100797186 | 1/2008 |
| KR | 1020080007245 | 1/2008 |
| KR | 1020090030385 | 3/2009 |
| KR | 1020090104427 | 10/2009 |

OTHER PUBLICATIONS

Loessner MJ. (2005) Bacteriophage endolysins—current state of research and applications. Curr. Opin. Microbiol., 8(4): 480-487.

\* cited by examiner

*Primary Examiner* — Chris R Tate
*Assistant Examiner* — Douglas F White
(74) *Attorney, Agent, or Firm* — Ballard Spahr LLP (57) ABSTRACT

The present invention relates to a composition for the treatment of ballast water containing bacteriophage capable of killing specific target bacteria as an active ingredient in order to eliminate or reduce bacteria including pathogenic bacteria present in ballast water, and a biological treatment method of ballast water.

2 Claims, 3 Drawing Sheets

COMPOSITION FOR THE TREATMENT OF BALLAST WATER CONTAINING BACTERIOPHAGE AS AN EFFECTIVE COMPONENT AND BIOLOGICAL METHOD WITH THE SAME FOR REMOVING BACTERIA PRESENT IN BALLAST WATER

CROSS REFERENCE TO RELATED APPLICATION

This application claims priority to Korean Patent Application No. 2008/0053743, filed Jun. 9, 2008, which application is incorporated by this reference in its entirety.

TECHNICAL FIELD

The present invention relates to a composition for the treatment of ballast water containing bacteriophage capable of killing specific target bacteria as an active ingredient in order to eliminate or reduce bacteria including pathogenic bacteria present in ballast water, and a biological treatment method of ballast water.

BACKGROUND ART

Ballast water is the sea water taken up and released by ships to keep their balance not to incline to one side when cargo is unloaded or loaded, or to prevent screw propeller from rising above the surface of water which makes sailing impossible. In this invention, ballast water indicates water both stored in ballast water tank (simply called 'tank' herein) and pumped up from the sea to store in the tank. In most cases, ballast water is sea water. According to International Maritime Organization (IMO), 3-5 billion tons of sea water is transported annually to other areas along with 7,000 species of organisms by ballasting and deballasting, which causes disturbance and even destruction of marine ecosystem.

The disturbance and destruction of marine ecosystem are not the only problem caused by ballast water. Public health is also threatened by epidemic pathogenic bacteria spread from one country to another. Such pathogenic bacteria transmitted through ballast water include microorganisms associated with waterborne disease.

Taking these matters seriously, "Ballast water Management Convention" is ready to come into effect from 2009 to intensify the supervision of ballast water. According to the "Ballast water Management Convention", every ship that is build from 2009 is forced to equip a treatment facility for killing marine organisms (marine species) and pathogenic bacteria present in ballast water before discharging by any means, for example using a chemicals or biocides or using organisms or biological mechanisms or by altering the chemical or physical characteristics of the ballast water, etc. That is, only those ships equipped with the ballast water treatment facility or ballast water exchanging facility are allowed to sail around the world. More precisely, according to the "Ballast water Management Convention", the amount of viable organisms of 10-50 μm in size in ballast water has to be up to 10 organisms per 1 ml for discharge and if viable organisms are as big as at least 50 μm, they has to be regulated up to 10 organisms per 1 m3. In the case of bacteria, the allowed number is similar to the number of bacteria included in the swimming beach, indicating the standard concerning bacteria is very strict. In the case of pathogenic bacteria, the allowed level is more strictly regulated, for example the number of toxicogenic *Vibrio cholerae* is limited to 1 cfu (colony forming unit: the number of colonies of bacteria)/100 ml, and the allowed number of intestinal *Enterococci* is less than 100 cfu/100 ml. The said bacteria are not the only targets of such regulation and all of pathogenic bacteria are targeted.

To meet the international standard, "Ballast Water Management Law" has been ready in Korea. According to this domestic law, it is basically prohibited for discharging ballast water in waters within the jurisdiction of Korea. It is also required to kill harmful marine organisms present in ballast water before discharging ballast water or only clean ballast water replaced in the open sea can be discharged without treatment. However, replacing ballast water with clean open-ocean water is not only inefficient but also not preferred because the population of viable organisms living in ocean water is already more than the international standard. So, this ballast water exchange is only good for temporary. Besides, replacing coastal water with open-ocean water might put a ship in danger of overturn if there is any mistake during ballast water exchange. In addition, during ballast water exchange, large area of a ship is emptied, which might result in severe default in structure or damage in the ship. Therefore, ballast water exchange in the ocean is not a preferable method.

There have been various attempts to develop methods for direct treatment of ballast water. Ballast water can be treated either before the ballast water enters the ballast tanks or before the ballast water is discharged from the ships. According to the conventional methods, sea water is pumped up and treated before being loaded in the ballast water tank. Macro-organisms present in sea water can be easily eliminated by filtration, so that most of the conventional methods use filtration to eliminate those macro-organisms. The techniques and methods under research now, therefore, target microorganisms present in ballast water, not viable macro-organisms. Thus, almost every conventional method consists of filtration for eliminating macro-organisms and sterilization for eliminating microorganisms. So, difference among the conventional methods is made by the skills to destroy microorganisms.

Chemical treatment and other methods have been developed to sterilize microorganisms.

Chemical treatment is exemplified by sterilization with hydrogen peroxide and chlorine dioxide (Korean Patent No. 10-0654105). However, using hydrogen peroxide causes acute toxicity and using chlorine dioxide causes safety problem. That is, using chemical compounds is strongly effective in treating microorganisms, particularly the effect lasts long enough since the chemical compounds remain in the tank to kill microorganisms, but these remaining chemical compounds become pollutants when ballast water is discharged out to the sea, causing a problem in maritime ecosystem.

To avoid utilizing such chemicals, alternatives have been proposed, for example a method using electrolysis that kills microorganisms with bactericides generated by electrolysis (Korean Patent No. 10-0776205 and No. 10-0597254); ozonization that kills viable organisms in ballast water by injecting ozone gas (Korean Patent Publication No. 10-2005-0104001 and No. 10-2008-0007245); UV irradiation that kills ocean microorganisms by UV irradiating (Korean Patent No. 10-0797186); high temperature treatment that kills ocean microorganisms by heating (Korean Patent Publication No. 2003-0004129); deoxygenation that kills microorganisms by making the environment not suitable for living (Korean Patent No. 10-0350409), etc. These methods have both merits and demerits. Among these methods, electrolysis and ozonization are focused. Herein, disadvantages of these methods, particularly of the above two, are explained. In the case of electrolysis, high voltage electricity is used, so that short circuit between a positive plate and a negative plate might happen and that has high risk of explosion. In addition, after long term use, various materials are accumulated on the surface of the plates, reducing the efficiency of electrolysis and requiring frequent replacement of the plates. By electrolysis, such chemicals as HOCl, NaOCl and NaOH are generated and used for sterilization but these chemicals are toxic and when they are released in the ocean, they are potentially harmful to the marine ecosystem. But, risks of these chemicals have been neglected due to the current technical limitation. In particular, the salt form of HOCl erodes the ballast water tank by forming chlorinated organic compounds. And, chlorine necessarily generated from electrolysis is another factor disturbing the maritime ecosystem. In the case of ozonization, treatment cost is high.

Electrolysis and ozonization, which do not directly use chemicals, are more pro-environmental methods than the methods using chemicals directly, but they require high price equipments and facilities, which can be a burden.

In addition to the high costs and disadvantages of each method above, the conventional methods designed not to use chemicals directly have a technical problem that is low treatment efficiency. The low efficiency problem is not only limited in electrolysis or ozonization but also observed in every conventional method developed to avoid direct chemical use. Again, almost every conventional method except direct chemical treatment has low efficiency problem. Such low efficiency is attributed to the following two reasons. One is that the conventional methods are designed to be only effective during the treatment in the inside of the equipment and they cannot give the residual effect in the ballast tanks. The other is that treatment time is too short to be efficient. According to the conventional methods designed to avoid direct chemical treatment, the treatment of ballast water is based on short-term treatment. Particularly, the conventional treatment is flow-through method and is performed during either the pumping of sea water or the discharging ballast water shortly not to delay the pumping or discharging. In reality, time cannot be waste for the ballast water treatment alone. Besides, the conventional flow-through methods are not adequate for full treatment of ballast water with enough time. Even this kind of inefficient and short conventional treatments can meet the international standard for bacteria which are regarded to be comparatively less harmful. However, they are not good enough for the treatment of pathogenic bacteria requiring more restricted standard. So, the methods capable of reducing bacteria to the required level are still insufficient for the treatment of pathogenic bacteria. Any bacteria, either general bacteria or pathogenic bacteria survived in ballast water can proliferate in the tank during sailing. Therefore, incomplete/inefficient ballast water treatment can cause a problem consequently.

To overcome this problem, alternative methods replacing the conventional methods have to be developed or methods capable of complementing the conventional methods have to be developed. The complementing method of the conventional method should be effective in the treatment of pathogenic bacteria and it is better if the method is pro-environmental.

The present inventors focused on bacteriophage capable of killing pathogenic bacteria. And the present inventors completed this invention based on the belief that bacteriophage capable of killing or reducing specific pathogenic bacteria can be a clue to develop a nature-friendly treatment method of ballast water.

Bacteriophage is a kind of virus-like microorganism infecting bacteria, which used to be called shortly 'phage'. Bacteriophages consist of an outer protein hull enclosing genetic materials. The genetic materials are single-stranded or double-stranded DNA or RNA. Bacteriophage needs a host to grow and every bacterium has its specific bacteriophage. When a bacteriophage infects a bacterium, bacteriophage lytic protein is synthesized at the end of the multiplication cycle in bacteriophage-infected cells. This lytic protein has the ability to directly cleave the bond in the peptidoglycan layer of the bacterial cell wall; the result of this activity is degradation of the rigid murein layer and release of newly assembled virions. Bacteriophage can kill bacteria by the above procedure (Curr. Opin. Microbiol. 8: 480-487, 2005).

Bacteriophage was first found by Twort, an English bacteriologist, in 1915 while he was studying on the phenomenon that *micrococcus* colony was decomposed by something and became clear. In 1917, d'Herelle, a French bacteriologist, found out during filtering the feces of a patient of shigellosis that there was something capable of decomposing *Shigella disentriae* in the feces. Then, he further studied and found out bacteriophage. Bacteriophage means 'eating bacteria'. Since then, bacteriophage of *shigella*, thypoid bacillus, and cholera bacillus have been continuously found out.

Recently, multidrug-resistant pathogenic bacteria are frequently reported because of excessive use or mis-use of antibiotics. Therefore, bacteriophage that is able to kill even multidrug-resistant pathogenic bacteria comes into the spotlight particularly in the field of medicine. Up to date, bacteriophage has been used to relieve or treat infectious disease via oral administration or injection. However, the present inventors were sure that such bacteriophage could be effectively used for eliminating or reducing pathogenic bacteria present in ballast water.

Numbers of papers and patent descriptions have been cited in this description and the citation is marked in parentheses. The descriptions of cited papers and patent documents are attached in this invention so that the art and text of this patent can be more clearly understood.

DISCLOSURE

Technical Problem

It is an object of the present invention to overcome the problems of the conventional methods including the technical problems.

It is another object of the present invention to provide a composition for the treatment of ballast water containing bacteriophage capable of killing bacteria including pathogenic bacteria present in ballast water as an active ingredient.

It is a further object of the present invention to provide a method for biological treatment of ballast water characteristically using the above composition to reduce or eliminate pathogenic bacteria or general bacteria present in ballast water.

It is also an object of the present invention to provide a complementing biological method of the conventional methods for treatment of ballast water by improving the treatment efficiency which has been a consistent problem of the conventional ballast water treatment methods.

It is also an object of the present invention to provide a method for biological treatment of ballast water that can supplement the weakness of the conventional ballast water treatment methods in relation to the treatment of pathogenic bacteria.

Technical Solution

To achieve the above objects, the present inventors selected some bacterial species from the pathogenic bacteria reported that they were present in ballast water as model species of pathogenic bacteria. Then, the inventors selected some target bacterial strains from the pathogenic bacteria isolated and confirmed previously as the bacterial strains of above model species by the present inventors. Next, the present inventors selected bacteriophage specifically capable of killing the pathogenic bacteria selected as targets from bacteriophages isolated previously by the inventors. So, the combination of such bacteriophage and selected bacteria represents various possible combinations of bacteriophage and its pathogenic bacteria targeted by the invention. In general, every bacterium has its own natural enemy bacteriophage. The present invention provides a composition capable of reducing or eliminating pathogenic bacteria present in ballast water containing bacteriophage that can be paired with the target bacteria as a natural enemy, and a method for biological treatment of ballast water using the composition.

The pathogenic bacteria selected above can represent all the pathogenic bacteria, so that the present invention can be applied in the treatment of any pathogenic bacteria. And, such pathogenic bacteria are also included in the criteria of bacteria, so that the present invention can be applied in any bacteria as well. Therefore, the present invention provides a composition for the treatment of ballast water to reduce or eliminate every bacteria present in ballast water, and a method for biological treatment of ballast water using the composition.

In this invention, a ship indicates every ship sailing in the ocean and includes a submarine, a floating ship, a floating platform, a floating storage equipment and other equipments for storage and loading/unloading.

Hereinafter, the present invention is described in detail.

The present inventors selected *Staphylococcus aureus*, *Salmonella enteritidis* and *Enterococcus faecalis* as model pathogenic bacteria. In fact, these pathogenic bacteria are present in ballast water (designated as bacteria present in seawater, according to Korea Food & Drug Administration report in 2003). *Staphylococcus aureus* is the major pathogenic bacterium causing skin infection and food poisoning. *Salmonella enteritidis* is one of causative bacteria of food poisoning, and *Enterococcus faecalis* is a major pathogenic bacterium causing endocarditis, cystitis, prostatitis, epididymitis, nervous system infection and sepsis.

Bacteriophages used in this invention were bacteriophage SAP-1, bacteriophage SEP-1 and bacteriophage EPA-1. Bacteriophage SAP-1 has been confirmed to have antimicrobial activity against *Staphylococcus aureus* by the present inventors in the previous studies, which was deposited at Korean Collection for Type Cultures (KCTC), Korea Institute of Biotechnology and Bioscience (KRIBB) on Jul. 18, 2007 (Accession No: KCTC 11153BP), and related study result was applied for patent and registered (Korean Patent No. 781669). Bacteriophage SEP-1 has been confirmed to have antimicrobial activity against *Salmonella enteritidis* by the present inventors in the previous studies, which was deposited at Korean Collection for Type Cultures (KCTC), Korea Institute of Biotechnology and Bioscience (KRIBB) on Aug. 21, 2007 (Accession No: KCTC 11173BP), and related study result was applied for patent (Korean Patent Application No. 10-2007-0095643). Bacteriophage EFA-1 has been confirmed to have antimicrobial activity against *Enterococcus faecalis* by the present inventors in the previous studies as well, which was also deposited at Korean Collection for Type Cultures (KCTC), Korea Institute of Biotechnology and Bioscience (KRIBB) on Feb. 26, 2008 (Accession No: KCTC 11289BP), and related study result was applied for patent (Korean Patent Application No. 10-2008-0029847).

Bacteriophage of the present invention is not limited and any bacteriophage can be used in this invention. Herein, three kinds of bacteriophages isolated and deposited by the present inventors were used as examples for convenience, but these are only examples and cannot limit the scope of the present invention. Bacteriophages usable in this invention are exemplified by bacteriophages of the Myoviridae family such as bacteriophages A, EW, K, Ph5, Ph9, Ph10, Ph13, P1, P2, P3, P4, P8, P9, P10, RG, SB-1, S3K, Twort, fSK311, f812, 06, 40, 58, 119, 130, 131, 200 and 1623; bacteriophages of the Siphoviridae family such as bacteriophages AC1, AC2, AC3, A6"C", A7, A8, A9"C", A10, b581, b595n, B3, B33, B39, BI-1, C22, CA-1, CA-2, CA-3, CA-4, CA-5, D, D3, D11, D37, D40, D62, D3112, F7, F10, g, gd, ge, gf, HK2, Hw12, Jb19, KF1, L39X35, L54a, M42, N1, N2, N3, N4, N5, N7, N8, N9, N10, N11, N12, N13, N14, N15, N16, OXN-32P, O6N-52P, P52, P87, Ph6, Ph12, Ph14, PCH-1, PC13-1, PC35-1, PH2, PH51, PH93, PH132, PMW, PM13, PM57, PM61, PM62, PM63, PM69, PM105, PM113, PM681, PM682, PO4, PP1, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-10, Pz, S1, S6, SD1, SL1, SL3, SL5, SM, UC-18, U4, U15, S1, S2, S3, S4, S5, Z1, Z4, X2, fC5, fC11, fC11-1, fC13, fC15, fMO, fX, f04, f11, f240, fB5-2, fD, fRE, ω, 2, 2F, 3A, 3B, 3C, 5, 6, 7, 7m, 11, 13, 13/441, 14, 15, 16, 20, 21, 24, 28, 28A, 29, 31, 31B, 37, 40, 42B, 42C, 42D, 42E, 44, 44A, 45, 47, 47A, 47C, 48, 49, 51, 52, 52A, 52B, 53, 54, 54X1, 55, 61, 69, 70, 71, 71A, 72, 73, 75, 76, 77, 78, 79, 80, 80a, 81, 82, 82A, 83A, 84, 85, 86, 88, 88A, 89, 90, 92, 93, 94, 95, 96, 101, 102, 105, 107, 108, 110, 111, 115, 129/16, 129-26, 130, 130A, 148, 155, 157, 157A, 160, 165, 174, 187, 198, 218, 222, 236, 242, 246, 249, 258, 269, 275, 275A, 275B, 295, 297, 309, 318, 342, 350, 351, 356, 357-1, 400-1, 456, 459, 471, 471A, 489, 581, 594n, 676, 898, 1139, 1154A, 1259, 1314, 1363/14, 1380, 1405, 1563, 2148, 2460, 2638A, 2638B, 2638C, 2731, 2792A, 2792B, 2818, 2835, 2848A, 3619, 5841 and 12100; and bacteriophages of the Podoviridae family such as bacteriophages A856, B26, CI-1, CI-2, C5, D, gh-1, F116, HF, H90, K5, K6, K104, K109, K166, K267, N4, N5, O6N-25P, PE69, Pf, PPN25, PPN35, PPN89, PPN91, PP2, PP3, PP4, PP6, PP7, PP8, PP56, PP87, PP114, PP206, PP207, PP306, PP651, Psp231a, Pssy401, Pssy9220, ps1, PTB2, PTB20, PTB42, PX1, PX3, PX10, PX12, PX14, PYO70, PYO71, R, SH6, SH133, tf, Ya5, Ya7, fBS, fKf77, f-MC, fmnF82, fPLS27, fPLS743, fS-1, 1, 2, 3, 4, 5, 6, 8, 9, 10, 11, 12, 12B, 13, 14, 15, 16, 17, 18, 19, 20, 21, 22, 23, 24, 25, 31, 53, 73, 119X, 145, 147, 170, 267, 284, 308 and 525, but not always limited thereto. In addition, such bacteriophages that can be purchased from American Type Culture Collection under the following accession numbers are also available, for example ATCC 12055-B1, ATCC 12055-B2, ATCC 12055-B3, ATCC 14205-B1, ATCC 14206-B1, ATCC 14207-B1, ATCC 14209-B1, ATCC 14210-B1, ATCC 14211-B1, ATCC 14212-B1, ATCC 14213-B1, ATCC 14214-B1, ATCC 15692-B2, ATCC 15692-B3, ATCC 25102-B1, ATCC BAA-26-B1, ATCC BAA-27-B1, ATCC BAA-28-B1, ATCC BAA-28-B2, ATCC BAA-29-B1, ATCC BAA-30-B1, ATCC BAA-31-B1, ATCC BAA-47-B1, ATCC BAA-79-B1, ATCC BAA-81-B1, ATCC BAA-81-B2, etc.

The possible target bacteria of the composition containing bacteriophage as an active ingredient of the present invention are every pathogenic bacterium that has cell wall. In this invention, *Staphylococcus aureus*, *Salmonella enteritidis* and *Enterococcus faecalis* were selected as representative examples, but as mentioned these are only examples and *Enterobacteriacae*, *Staphylococcus* genus, *Enterococcus*,

*Streptococcus, Staphylococcus epidermidis,* coagulase-negative *staphylococci, Pseudomonas aeruginosa, Klebsiella pneumoniae, Escherichia coli, Enterococcus faecalis, Enterococcus faecium, Providencia stuartii, Proteus mirabilis, Morganella morganii, Acinetobacter calcoaceticus, Enterobacter aerogenes, Streptococcus agalactiae, Streptococcus avium, Streptococcus bovis, Streptococcus durans, Streptococcus faecalis, Streptococcus pneumoniae, Streptococcus pyogenes, Streptococcus suis, Streptococcus viridans, Streptococcus salivarius, Burkholderia cepacia, Stenotrophomonas maltophilia, Acaligenes xylosoxidans,* non-tuberculous *mycobacteria, Mycobacterium bovis, Mycobacterium smegmatis, Mycobacterium tuberculosis, Burkholderia multivorans, Burkholderia stablis,* and *Burkholderia vietnamesis* can also be used as targets of the present invention, but not always limited thereto, either.

The present invention is not only applied in pathogenic bacteria but also applied in general bacteria. All of them have cell walls and their own natural enemies, so that they can be targeted by the present invention.

The composition of the present invention containing bacteriophage as an active ingredient can be formulated as a liquid composition, particularly as a water-soluble liquid composition and can also be formulated as a mixture with an organic solvent or as a suspension. The composition of the present invention can also be formulated as a solid composition using dried bacteriophage. The liquid composition is exemplified by solution in oil or water, suspension and emulsion, which can additionally include a dispersing agent or a stabilizer. The solid composition is exemplified by powders, granules, tablets or capsules, which can additionally include a dispersing agent or a stabilizer.

The liquid composition of the present invention contains bacteriophage at the titer of $1\times10^3$-$1\times10^{20}$ pfu/ml, and preferably at the titer of $1\times10^6$-$1\times10^{15}$ pfu/ml. The titer of bacteriophage in the liquid composition of the present invention can be regulated according to the purpose of use, which can be determined without any difficulty by those in the art.

The solid composition of the present invention can be prepared by various drying methods generally used, and preferably by freeze-drying.

The content of dried bacteriophage in the solid composition can be chosen by those in the art without restrictions.

The liquid or solid composition of the present invention can contain one kind of bacteriophage or at least two different bacteriophages. The composition containing only one kind of bacteriophage is suitable for reducing and eliminating a specific kind of bacterium and the composition containing at least two kinds of bacteriophages is suitable for reducing and eliminating two or more kinds of bacteria. In reality, it is necessary to treat different kinds of bacteria at the same time. Therefore, when the composition containing one kind of bacteriophage is used, some other compositions each containing different bacteriophages are preferably co-treated. In the meantime, when the composition containing at least two different kinds of bacteriophages is used, it is not necessary to co-treat with many different compositions. What kind of bacteriophage or how many of them will be included is only a matter of decision in the application of the present invention.

As an example, the composition containing as many bacteriophages as possible, as a form of cocktail, is preferred. Particularly, to treat ballast water containing non-specific, various kinds of bacteria, it is preferred for the composition containing as many bacteriophages as possible so as to eliminate and reduce many different pathogenic bacteria. However, it is impossible for the composition of the present invention to contain unlimited bacteriophages. Therefore, it is preferably suggested that firstly, examining kinds of bacteria present in ballast water samples collected from different ships is performed and then particularly haniful pathogenic microorganisms are selected among all the bacteria identified in the ballast water samples, then, the composition containing specific bacteriophages capable of killing those selected pathogenic microorganisms is prepared. Of course, it is not always necessary to include bacteriophage specifically against the bacteria confirmed to be included in ballast water. There is always possibility that any or every bacteria can be included in ballast water even if it is not detected in pre-examining, so the composition can contain bacteriophage that is paired with non-detected bacterium as well.

The composition of the present invention, either prepared as a liquid composition or a solid composition, can additionally include other components, in addition to bacteriophage. The additional components can be any general compound such as lactose, dextrose, sucrose, sorbitol, mannitol, starch, acacia rubber, calcium phosphate, alginate, gelatin, calcium silcate, microcrystalline cellulose, polyvinyl pyrrolidone, cellulose, water, syrup, methyl cellulose, methylhydroxybenzoate, propylhydroxybenzoate, talc, magnesium stearate and mineral oil, but not always limited thereto. The composition of the present invention can also include sweetening agents, suspensions and preservatives, additionally. In particular, to prepare a solid composition, the above components can be mixed with dried bacteriophage or they can be added to liquid bacteriophage suspension and then the mixture is dried. The two methods can be co-used to prepare a solid composition.

The composition of the present invention can be injected to a proper package and packed by the conventional method well known to those in the art. The composition of the present invention can be formulated by using a carrier and/or an excipient according to the conventional method that can be performed easily by those in the art, as a unit dosage or as a bulk.

The composition of the present invention can be directly added to ballast water (herein, ballast water indicates both the sea water stored in ballast water tank and the sea water pumped up from the ocean but not stored in the tank yet) or diluted or dissolved in a proper solvent including water before added. That is, the composition can be stored at a high titer and right before use it can be diluted properly.

A proper dose of the composition of the present invention can be determined by considering the amount of ballast water, kinds of target microorganisms and population per unit volume, kinds of bacteriophages used as an active ingredient and their contents, methods for formulating the composition, treatment methods, etc. To those in the art, it is easy to determine the effective dose of the composition by simple pre-test. As explained hereinbefore, the titer of bacteriophage in ballast water tank is preferably limited to a specific titer, which is generally $1\times10^1$-$1\times10^8$ pfu/m3 and more preferably $1\times10^2$-$1\times10^6$ pfu/m3. However, the titer of bacteriophage can vary from pathogenic microorganisms and their partner phages. In nature, there are numbers of pairs of bacteria and bacteriophages, so it is very difficult to provide a specific titer suitable for every pair.

In application of the present invention, the present invention can be applied alone to treat ballast water, but it is more preferred to apply the invention together with the conventional methods to treat ballast water, because the final goal of ballast water treatment is to eliminate every organism in ballast water. The organism herein includes pathogenic microorganisms, eggs, and cyst or larvae detected in planktonic stage of life cycle of a sea living thing. Considering that the method of the present invention is very effective in eliminating pathogenic bacteria and the conventional methods are effective in eliminating various different sea organisms but not in eliminating pathogenic bacteria, the co-treatment of the method of the present invention and the conventional methods can be more effective. The standard of limitation on pathogenic microorganisms is stricter than that on the general bacteria. Therefore, when the method of the present invention is additionally applied, after the conventional ballast water treatment, it is not difficult to meet the strict standard of limitation of pathogenic microorganisms in ballast water without modification of the conventional methods.

In most cases, the conventional methods treat ballast water before putting the sea water in the tank, but theoretically it is not a problem to treat ballast water before loading in the tank or before discharging out to the sea. Therefore, the proper stage of application of the present invention is as follows, but not always limited thereto.

First, in the case that the method of the present invention is co-used with the conventional method treating ballast water before discharging the water out to the sea, the composition of the present invention is added to the ballast water tank for eliminating and reducing pathogenic bacteria and then ballast water treatment by the conventional method is performed sequently, followed by discharging. It is also possible to treat ballast water with the conventional method first and then with the method of the invention later on. However, higher treatment effect is expected when the method of the present invention is performed ahead of the conventional treatment. When the ballast water is treated with the method of the present invention first, it is advantageous because more time is given for enough treatment effect and the treatment can be done at any time during sailing prior to the treatment of ballast water with the conventional method.

In the case that the ballast water is treated by the conventional method before loading in the tank, the method of the present invention can be performed thereto either before or after the conventional treatment or at the same time with the conventional method. However, it is preferred to treat the ballast water with the method of the present invention after treating the ballast water with the conventional method. Because when the method of the present invention is carried out before the conventional method is performed, this cannot give enough time for the treatment of ballast water by the method of the present invention to give satisfactory effect and no advantage of free-treatment at any time. In addition, the effective bacteriophage might be destroyed by the conventional treatment. However, if the composition of the present invention is added to ballast water treated by the conventional treatment, there is no risk of destroying effective bacteriophage and therefore the effective ingredient stays longer in the ballast water tank to work continuously. The residual effect contributes greatly to prevent secondary contamination generated during sailing by the proliferation of non-treated remaining bacteria (this contamination is not by the new invasion of a foreign bacterium into the tank but by the proliferation of the non-treated, remaining bacteria in the tank, but it is called as secondary contamination herein).

Advantageous Effect

The present invention provides a composition for the treatment of ballast water containing bacteriophage capable of killing pathogenic bacteria or general bacteria as an active ingredient in order to eliminate or reduce bacteria including pathogenic bacteria present in ballast water, and a biological treatment method of ballast water using the same. The treatment method of ballast water of the present invention can effectively eliminate almost every bacterium that has cell wall, for example of toxicogenic *Vibrio cholerae, Escherichia coli*, intestinal *Enterococci* and other general bacteria, etc, in ballast water. The method of the present invention does not need special equipments, suggesting it is less expensive, and consists of simple processes but brings higher effect with simple treatment. Besides, the treatment of pathogenic bacteria by the method of the present invention is highly efficient, so that this method is still available even after the international standard of limitation of bacteria present in ballast water will be tightened more. The present invention also provides a pro-environmental method for treating ballast water since it is based on the natural enemy relation. There is no need to spare room in a ship for equipments or facilities for the treatment according to the present invention. Only a small amount of the composition of the present invention can be effective because the active bacteriophage can auto-proliferate as long as there is a host pathogenic microorganism (to reach the effective titer) and eventually be capable of killing the pathogenic microorganism and therefore the content of the composition of the present invention is not necessarily regulated, which makes the treatment easier. Besides, owing to the residual effect, the secondary contamination in the ballast water tank is greatly prevented. As mentioned hereinbefore, the present invention can be co-used with the conventional methods, providing totally effective solution altogether. That is, the present invention can complement the weakness of the conventional methods which is not efficient in eliminating pathogenic microorganisms when it is co-used with the conventional method. Considering that the restriction on pathogenic microorganisms will be stricter, the use of the method of the present invention will be increasing.

DESCRIPTION OF DRAWINGS

The application of the preferred embodiments of the present invention is best understood with reference to the accompanying drawings, wherein:

In FIG. 1, <−bacteriophage> indicates no treatment, and <+bacteriophage> indicates treatment with the composition containing bacteriophage of the present invention as an active ingredient. The number shown over the bar graph indicates the number of colonies formed on each Petri-dish (the number of colonies generated in 1 ml of ballast water), which was the mean value calculated from all the samples taken from 5 ships. There was no significant difference among the results from samples taken from 5 ships, so standard deviation is not given herein.

FIG. 2 is a set of photographs of Petri-dishes showing the colonies of *Staphylococcus aureus* formed thereon. In this Figure, the left side shows ballast water treated with nothing (corresponding to <−bacteriophage> in FIG. 1) and the right side shows ballast water treated with the composition of the present invention (corresponding to <+bacteriophage> in FIG. 1).

In FIG. 3, <−bacteriophage> indicates no treatment, and <+bacteriophage> indicates treatment with the composition containing bacteriophage of the present invention as an active ingredient. The number shown over the bar graph indicates the number of colonies formed on each Petri-dish (the number of colonies generated in 1 ml of ballast water), which was the mean value calculated from all the samples taken from 5 ships. There was no significant difference among the results from samples taken from 5 ships, so standard deviation is not given herein.

In FIG. 4, <−bacteriophage> indicates no treatment, and <+bacteriophage> indicates treatment with the composition containing bacteriophage of the present invention as an active ingredient. The number shown over the bar graph indicates the number of colonies formed on each Petri-dish (the number of colonies generated in 1 ml of ballast water), which was the mean value calculated from all the samples taken from 5 ships. There was no significant difference among the results from samples taken from 5 ships, so standard deviation is not given herein.

In FIG. 5, <−bacteriophage> indicates no treatment, and <+bacteriophage> indicates treatment with the composition containing bacteriophage of the present invention as an active ingredient. The number shown over the bar graph indicates the number of colonies formed on each Petri-dish (the number of colonies generated in 1 ml of ballast water), which was the mean value calculated from all the samples taken from 5 ships. There was no significant difference among the results from samples taken from 5 ships, so standard deviation is not given herein. FIG. 5(a) illustrates the result of application to *Staphylococcus aureus*, FIG. 5(b) illustrates the result of application to *Salmonella enteritidis* and FIG. 5(c) illustrates the result of application to *Enterococcus faecalis*.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Compositions Containing Different Bacteriophages as Active Ingedients The present inventors prepared the composition #1 applicable for *Staphylococcus aureus* using bacteriophage SAP-1 (Accession No: KCTC 11153BP) isolated previously by the present inventors. The present inventors also prepared the composition #2 applicable for *Salmonella enteritidis* using bacteriophage SEP-1 (Accession No: KCTC 11173BP) isolated previously by the present inventors. The present inventors also prepared the composition #3 applicable for *Enterococcus faecalis* by using bacteriophage EFA-1 (Accession No: KCTC 11289BP) isolated previously by the present inventors.

Particularly, to prepare SAP-1 bacteriophage suspension, *Staphylococcus aureus* was inoculated into 10 ml of TSB (Tryptic Soy Broth) medium (casein digest, 17 g/L; soybean digest, 3 g/L; dextrose, 2.5 g/L; NaCl, 5 g/L; dipotassium phosphate, 2.5 g/L), followed by shaking culture at 37° C. for overnight. Next day, 500 µl of *Staphylococcus aureus* culture broth and 1 ml of bacteriophage SAP-1 suspension were inoculated to 4 ml of fresh TSB medium. The mixture was cultivated at 37° C. for at least 5 hours. Upon completion of the culture, the culture broth was centrifuged at 5,000 rpm for 10 minutes to obtain supernatant. The obtained supernatant was filtered by 0.45 µm filter and 1.5 ml of *Staphylococcus aureus* culture broth was added to the filtrate. The mixture was shaking-cultured at 37° C. for overnight. On the next day, the culture broth was centrifuged at 5,000 for 10 minutes to obtain supernatant and the obtained supernatant was filtered by 0.45 µm filter. 2 ml of *Staphylococcus aureus* culture broth was added to the filtrate, followed by shaking-culture at 37° C. for 4 hours. Upon completion of the culture, the culture broth was centrifuged at 5,000 rpm for 10 minutes to obtain supernatant. The supernatant was filtered by 0.45 µm filter to obtain the primary bacteriophage suspension. The bacteriophage suspension was that bacteriophages were suspended in TSB medium. To replace the medium with physiologically acceptable medium, it was treated as follows. Polyethyleneglycol (PEG) precipitation buffer [20% (w/v) PEG 8,000; 2.5 M NaCl] was added to the primary bacteriophage suspension by 6 times the volume of the bacteriophage suspension. After mixing well, it stood at 4° C. for overnight. On the next day, the mixture was centrifuged at 8,000 rpm for 15 minutes to obtain bacteriophage pellet. The pellet was resuspended in phosphate buffered saline (PBS). The prepared bacteriophage suspension was properly diluted (10-14-10-18) with PBS, followed plaque assay to determine the titer of bacteriophage of the bacteriophage suspension. Based on the determined bacteriophage titer of the bacteriophage suspension, the titer of bacteriophage was adjusted at the final titer of 1010 pfu/ml using PBS. This was the final SAP-1 bacteriophage suspension, which would be the composition #1 of the present invention.

*Salmonella enteritidis*-specific bacteriophage SEP-1 suspension was also prepared by the same manner as performed to prepare bacteriophage SAP-1 suspension in the above, except *Salmonella enteritidis* was used instead of *Staphylococcus aureus*. Particularly, from the above method of preparing bacteriophage SAP-1 suspension, the application of bacteriophage SAP-1 was replaced with the application of bacteriophage SEP-1 and *Staphylococcus aureus* was replaced with *Salmonella enteritidis*. The resultant composition was the composition #2 of the present invention.

*Enterococcus faecalis*-specific bacteriophage EFA-1 suspension was also prepared by the same manner as performed to prepare bacteriophage SAP-1 suspension in the above, except *Enterococcus faecalis* was used instead of *Staphylococcus aureus*. Particularly, from the above method of preparing bacteriophage SAP-1 suspension, the application of bacteriophage SAP-1 was replaced with the application of bacteriophage EFA-1 and *Staphylococcus aureus* was replaced with *Enterococcus faecalis*. The resultant composition was the composition #3 of the present invention.

The composition #4 of the present invention was also prepared by mixing the composition #1, composition #2 and composition #3 at the volume ratio of 1:1:1.

Example 2

Treatment of Ballast Water with the Compositions of the Present Invention <2-1> Application of Composition #1 Prepared by Using *Staphylococcus aureus*-Specific Bacteriophage SAP-1

Ballast water was taken from 5 ships, by 100 ml per each ship. 30 ml of each ballast water sample was poured in each sterilized Erlenmeyer flask in a clean bench. The flask was sealed with a sterilized lid. 2 samples per each ship, total 10 samples were prepared. One of the two samples from each ship was treated with nothing and just left at room temperature. The other sample was treated by adding 10 μl of the composition #1 which had been 107 fold diluted with water, and then left at room temperature with the mouth of the flask closed. After one day, 1 ml of each was taken, which was spread on Baird-Parker agar medium, the *Staphylococcus aureus* selection medium, followed by culture in a 37° C. incubator for overnight. On the next day, the number of colonies formed on the solid medium was counted.

Figure 1:
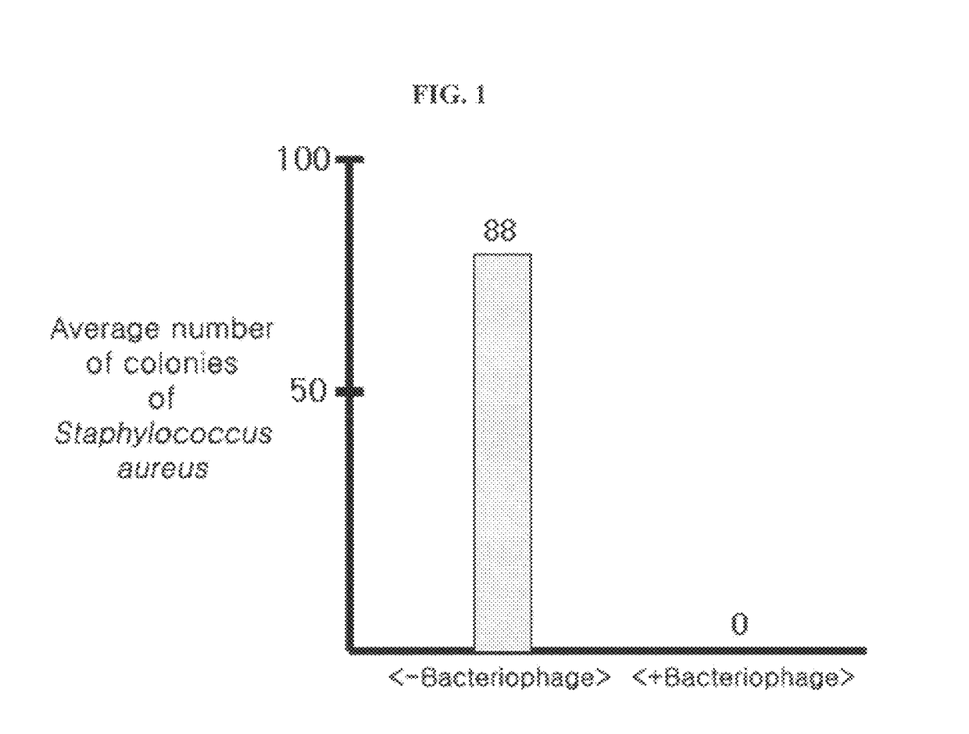
FIG. 1 illustrates the results of application of the composition #1 of the present invention containing *Staphylococcus aureus*-specific bacteriophage as an active ingredient to *Staphylococcus aureus*.
Figure 2:
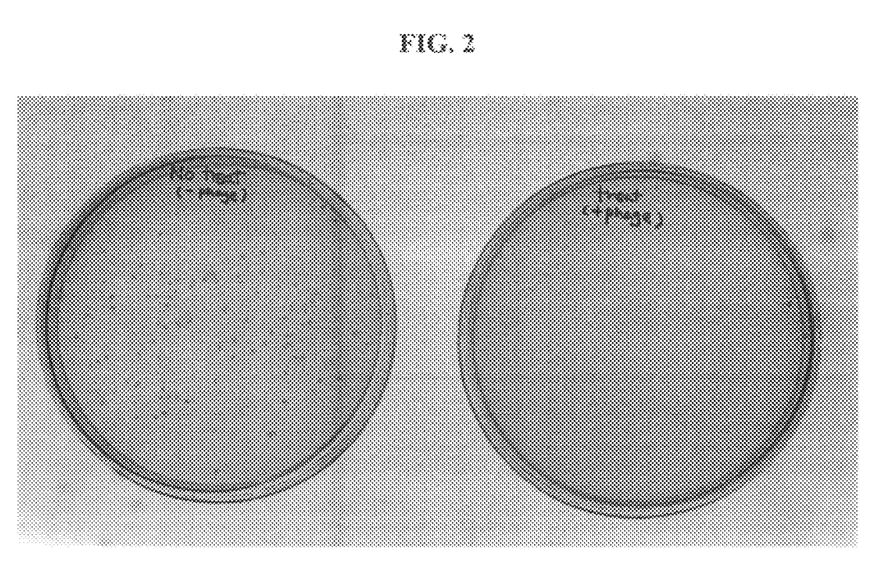

As a result, the controls treated with nothing showed *Staphylococcus aureus* colonies, while the other samples treated with the composition containing bacteriophage as an active ingredient did not show any *Staphylococcus aureus* colony. The results are shown in FIG. 1. Pictures of Petri-dishes illustrating colony formation are shown in FIG. 2 to help understanding. When the time of standing at room temperature was adjusted to one hour or two hours, the results were consistent with that of this example which left the sample for one day, so the results are not shown herein. Therefore, it was confirmed that the treatment with the composition of the present invention containing bacteriophage SAP-1 is very effective in reducing or eliminating *Staphylococcus aureus* in ballast water.

<2-2> Application of Composition #2 Prepared by Using *Salmonella enteritidis*-Specific Bacteriophage SEP-1

Ballast water was taken from 5 ships, by 100 ml per each ship. 30 ml of each ballast water sample was poured in each sterilized Erlenmeyer flask in a clean bench. The flask was sealed with a sterilized lid. 2 samples per each ship, total 10 samples were prepared. One of the two samples from each ship was treated with nothing and just left at room temperature. The other sample was treated by adding 10 μl of the composition #2 which had been 107 fold diluted with water, and then left at room temperature with the mouth of the flask closed. After one day, 1 ml of each was taken, which was spread on *Salmonella-Shigella* (SS) agar medium, the *Salmonella* selection medium, followed by culture in a 37° C. incubator for overnight. On the next day, the number of colonies formed on the solid medium was counted.

Figure 3:
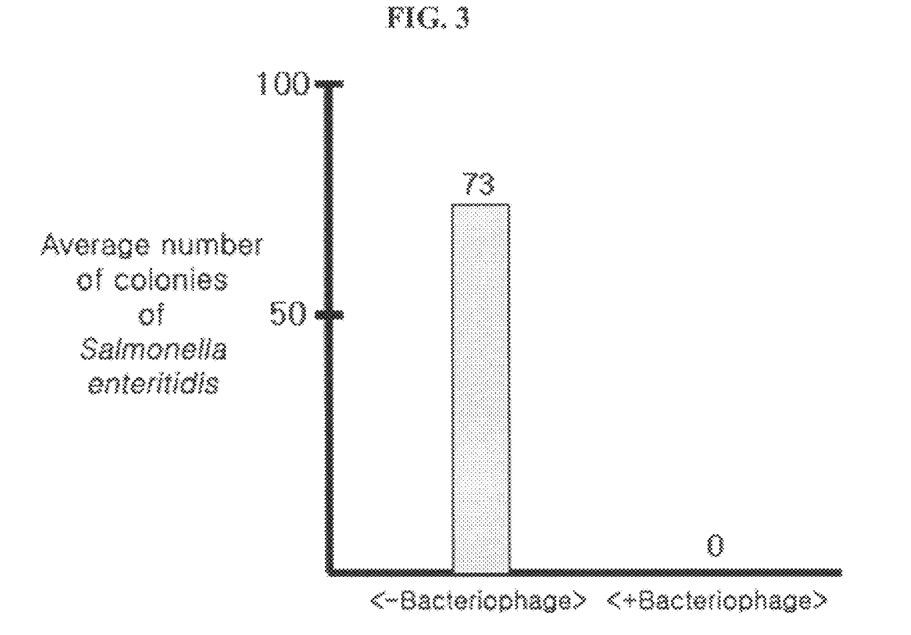
FIG. 3 illustrates the results of application of the composition #2 of the present invention containing *Salmonella enteritidis*-specific bacteriophage as an active ingredient to *Salmonella enteritidis*.

As a result, the controls treated with nothing showed *Salmonella enteritidis* colonies, while the other samples treated with the composition containing bacteriophage as an active ingredient did not show any *Salmonella enteritidis* colony. The results are shown in FIG. 3. When the time of standing at room temperature was adjusted to one hour or two hours, the results were consistent with that of this example which left the sample for one day, so the results are not shown herein. Therefore, it was confirmed that the treatment with the composition of the present invention containing bacteriophage SEP-1 is very effective in reducing or eliminating *Salmonella enteritidis* in ballast water.

<2-3> Application of Composition #3 Prepared by Using *Enterococcus faecalis*-Specific Bacteriophage EFA-1

Ballast water was taken from 5 ships, by 100 ml per each ship. 30 ml of each ballast water sample was poured in each sterilized Erlenmeyer flask in a clean bench. The flask was sealed with a sterilized lid. 2 samples per each ship, total 10 samples were prepared. One of the two samples from each ship was treated with nothing and just left at room temperature. The other sample was treated by adding 10 μl of the composition #3 which had been 107 fold diluted with water, and then left at room temperature with the mouth of the flask closed. After one day, 1 ml of each was taken, which was spread on Bile Esculin Azide agar medium, the *Enterococcus faecalis* selection medium, followed by culture in a 37° C. incubator for overnight. On the next day, the number of colonies formed on the solid medium was counted.

Figure 4:
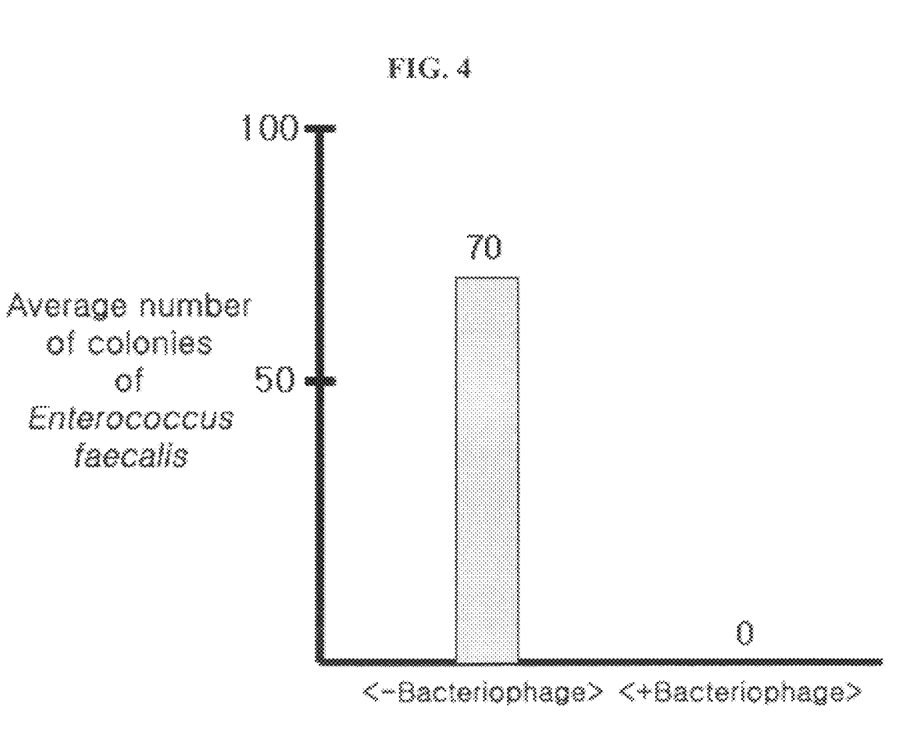
FIG. 4 illustrates the results of application of the composition #3 of the present invention containing *Enterococcus faecalis*-specific bacteriophage as an active ingredient to *Enterococcus faecalis*.

As a result, the controls treated with nothing showed *Enterococcus faecalis* colonies, while the other samples treated with the composition containing bacteriophage as an active ingredient did not show any *Enterococcus faecalis* colony. The results are shown in FIG. 4. When the time of standing at room temperature was adjusted to one hour or two hours, the results were consistent with that of this example which left the sample for one day, so the results are not shown herein. Therefore, it was confirmed that the treatment with the composition of the present invention containing bacteriophage EFA-1 is very effective in reducing or eliminating *Enterococcus faecalis* in ballast water.

<2-4> Application of Composition #4 Prepared by Using Bacteriophage Mixed Suspension Ballast water was taken from 5 ships, by 100 ml per each ship. 30 ml of each ballast water sample was poured in each sterilized Erlenmeyer flask in a clean bench. The flask was sealed with a sterilized lid. 2 samples per each ship, total 10 samples were prepared. One of the two samples from each ship was treated with nothing and just left at room temperature. The other sample was treated by adding 30 μl of the composition #4 which had been 107 fold diluted with water, and then left at room temperature with the mouth of the flask closed. After one day, 1 ml of each sample was taken three times. The first 1 ml was spread on Baird-Parker agar medium, the *Staphylococcus aureus* selection medium, the second 1 ml was spread on *Salmonella-Shigella*(SS) agar medium, the *Salmonella* selection medium, and the last 1 ml was spread on Bile Esculin Azide agar medium, the *Enterococcus faecalis* selection medium, followed by culture in a 37° C. incubator for overnight. On the next day, the number of colonies formed on the solid medium was counted.

Figure 5:
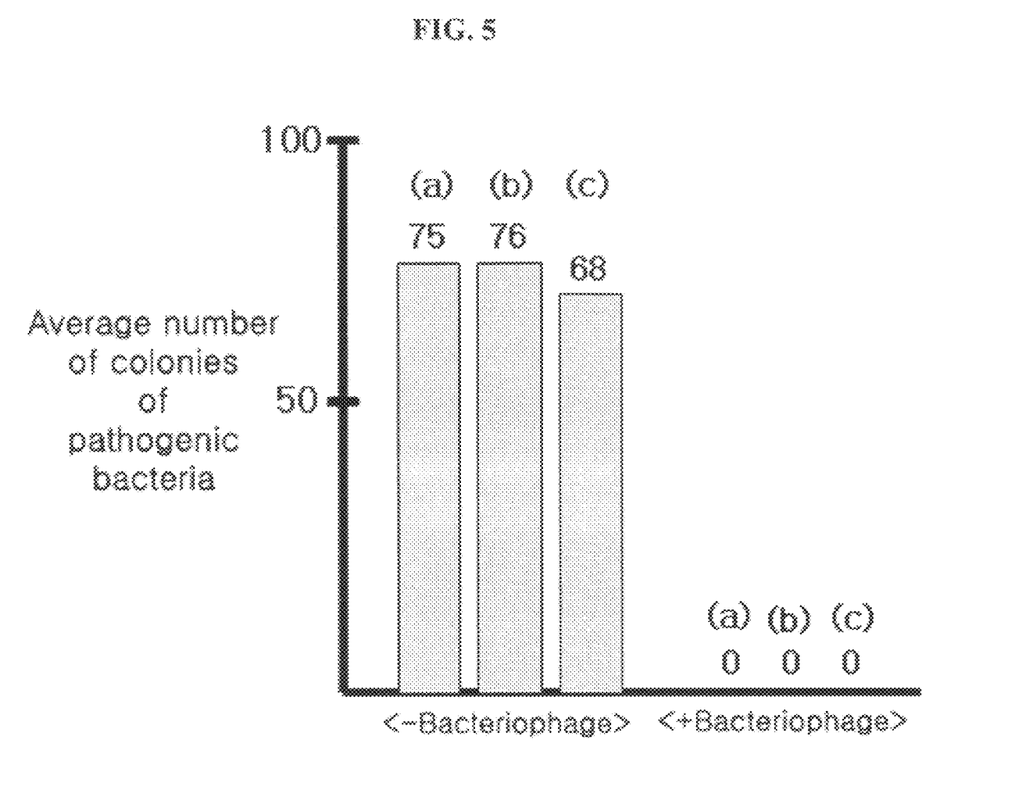
FIG. 5 illustrates the results of application of the composition #4 of the present invention containing *Staphylococcus aureus*, *Salmonella enteritidis* and *Enterococcus faecalis*-specific bacteriophages to each of them.

As a result, the controls treated with nothing showed colony formation of corresponding pathogenic microorganism on each selection medium, while the samples treated with the composition containing bacteriophage as an active ingredient did not show any pathogenic microorganism colony in every selection medium. The results are shown in FIG. 5. From the above results, it was confirmed that the treatment with the composition of the present invention containing different bacteriophages is effective in reducing or eliminating different pathogenic microorganisms in the ballast water at the same time.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A biological method for the treatment of ballast water, wherein the method comprises adding a composition that contains a bacteriophage selected from the group consisting of bacteriophage SEP-1 (Accession No, KCTC 11173BP) and bacteriophage EFA-1 (Accession No. KCTC 11289BP) as an active ingredient to the ballast water, wherein the final titer of the bacteriophage is $1\times10^1$-$1\times10^8$ pfu/m3.

2. The biological method for the treatment of ballast water according to claim 1, wherein the composition comprises one or more additional bacteriophages.

* * * * *